US00PP30198P2

(12) United States Plant Patent
Spruit

(10) Patent No.: US PP30,198 P2
(45) Date of Patent: Feb. 12, 2019

(54) ***ALOCASIA* PLANT NAMED 'AARALZE001'**

(50) Latin Name: *Alocasia zebrina*
Varietal Denomination: AARALZE001

(71) Applicant: Adrianus Theodorus Spruit, Aarlanderveen (NL)

(72) Inventor: Adrianus Theodorus Spruit, Aarlanderveen (NL)

(73) Assignee: Aardam B.V., Aarlanderveen (NL)

( * ) Notice: Subject to any disclaimer, the term of this patent is extended or adjusted under 35 U.S.C. 154(b) by 0 days.

(21) Appl. No.: 15/732,276

(22) Filed: Oct. 17, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Alocasia* plant named 'AARALZE001', characterized by its compact, upright to outwardly arching and uniform plant habit; moderately vigorous growth habit; moderately rapid growth rate; dark green-colored leaves; and greyed green-colored petioles that are transversely marked with dark greyed green to black-colored marbling.

2 Drawing Sheets

Botanical designation: *Alocasia zebrina.*
Cultivar denomination: 'AARALZE001'.

BACKGROUND OF THE INVENTION

The present invention relates to a new and distinct cultivar of *Alocasia* plant, botanically known as *Alocasia zebrina*, common referred to as Elephant's Ear Plant and hereinafter referred to by the name 'AARALZE001'.

The new *Alocasia* plant is a naturally-occurring whole plant mutation of an unnamed selection of *Alocasia zebrina*, not patented. The new *Alocasia* plant was discovered and selected by the Inventor in November, 2015 as a single plant within a population of plants of the mutation parent selection in a controlled greenhouse environment in Aarlanderveen, The Netherlands.

Asexual reproduction of the new *Alocasia* plant by vegetative cuttings in a controlled greenhouse environment in Aarlanderveen, The Netherlands since June, 2016 has shown that the unique features of this new *Alocasia* plant are stable and reproduced true to type in successive generations of asexual reproduction.

SUMMARY OF THE INVENTION

Plants of the new *Alocasia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'AARALZE001'. These characteristics in combination distinguish 'AARALZE001' as a new and distinct *Alocasia* plant:

1. Compact, upright to outwardly arching and uniform plant habit.
2. Moderately vigorous growth habit.

3. Moderately rapid growth rate.
4. Dark green-colored leaves.
5. Greyed green-colored petioles that are transversely marked with dark greyed green to black-colored marbling.

Plants of the new *Alocasia* differ primarily from plants of the mutation parent selection in plant habit as plants of the new *Alocasia* are much more compact than plants of the mutation parent selection.

Plants of the new *Alocasia* can be compared to plants of *Alocasia zebrina* 'Reticulata', not patented. In side-by-side comparisons plants of the new *Alocasia* differ primarily from plants of 'Reticulata' in the following characteristics:

1. Leaves of plants of the new *Alocasia* are shorter and broader than leaves of plants of 'Reticulata'.
2. Leaves of plants of the new *Alocasia* are solid green in color whereas leaves of plants of 'Reticulata' are variegated.

BRIEF DESCRIPTION OF THE PHOTOGRAPHS

The accompanying photographs illustrate the overall appearance of the new *Alocasia* plant showing the colors as true as it is reasonably possible to obtain in colored reproductions of this type. Colors in the photographs may differ slightly from the color values cited in the detailed botanical description which accurately describe the colors of the new *Alocasia* plant.

The photograph on the first sheet is a side perspective view of a typical plant of 'AARALZE001' grown in a container.

The photograph on the second sheet is a close-up view of typical leaf petioles of 'AARALZE001'.

DETAILED BOTANICAL DESCRIPTION

The aforementioned photographs and following observations and measurements describe plants grown in 14-cm containers in Aarlanderveen, The Netherlands during the winter in a glass-covered greenhouse. Plants were grown under environmental conditions and cultural practices which approximate those generally used in commercial *Alocasia* production. During the production of the plants, day temperatures ranged from 20° C. to 28° C. and night temperatures ranged from 18° C. to 22° C. Plants were six months from planting when the photographs and the detailed description were taken. In the following description, color references are made to The Royal Horticultural Society Colour Chart, 2015 Edition, except where general terms of ordinary dictionary significance are used.

Botanical classification: *Alocasia zebrina* 'AARALZE001'.

Parentage: Naturally-occurring whole plant mutation of an unnamed selection of *Alocasia zebrina*, not patented.

Propagation:

*Type*.—By vegetative cuttings.

*Time to initiate roots, summer*.—About 21 days at temperatures about 20° C. to 30° C.

*Time to initiate roots, winter*.—About 31 days at temperatures about 20° C. to 25° C.

*Time to produce a rooted young plant, summer*.—About 140 days at temperatures about 22° C. to 30° C.

*Time to produce a rooted young plant roots, winter*.—About 200 days at temperatures about 20° C. to 25° C.

*Root description*.—Medium in thickness to thick, fleshy; typically white to light brown in color, actual color of the roots dependent on substrate composition, water quality, fertilizer, substrate temperature and age of roots.

*Rooting habit*.—Low branching; moderately dense.

Plant description:

*Plant and growth habit*.—Compact, upright to outwardly arching and uniform plant habit; moderately vigorous growth habit and moderately rapid growth rate.

*Plant height, from soil level to top of leaf plane*.—About 27.4 cm.

*Plant diameter or spread*.—About 26.4 cm.

*Clumping habit*.—Plants of the new *Alocasia* are not freely clumping with typically a single clump developing per container.

Leaf description:

*Arrangement*.—Alternate; simple.

*Length*.—About 17.9 cm.

*Width*.—About 9.8 cm.

*Shape*.—Triangular.

*Apex*.—Apiculate.

*Base*.—Hastate to sagittate.

*Margin*.—Entire; moderately undulate.

*Texture and luster, upper surface*.—Smooth, glabrous; slightly glossy.

*Texture and luster, lower surface*.—Smooth, glabrous; moderately glossy.

*Venation pattern*.—Pinnate.

*Color*.—Developing leaves, upper surface: Darker than between NN137A and 139A. Developing leaves, lower surface: Close to between 147B and 191B. Fully expanded leaves, upper surface: Close to between NN137A and 147A; venation, close to between 139A and 147A. Fully expanded leaves, lower surface: Close to 138A to 138B; venation, close to 138B to 138C.

*Petioles*.—Aspect: Mostly erect, outwardly arching with development. Length: About 20.4 cm. Diameter, distal: About 4 mm. Diameter, mid-section: About 6 cm. Diameter, proximally: About 9 cm. Strength: Moderately strong; flexible. Texture and luster: Smooth, glabrous; slightly glossy. Color: Ground color, close to 196A to 196B; transversely marbled with close to between N189A and 203C. Wing length: About 7.9 cm. Wing diameter, base: About 3.5 mm. Wing color, inner and outer surfaces: Ground color, close to 196A to 196B; transversely marbled with close to between N189A and 203C.

Inflorescence description: Inflorescence development has not been observed on plants of the new *Alocasia* to date.

Disease & pest resistance: Plants of the new *Alocasia* have not been observed to be resistant to pathogens or pests common to *Alocasia* to date.

Temperature tolerance: Plants of the new *Alocasia* have been observed to tolerate temperatures ranging from about 5° C. to about 40° C. and to be suitable for USDA Hardiness Zones 11 to 13.

It is claimed:

1. A new and distinct *Alocasia* plant named 'AARALZE001' as illustrated and described.

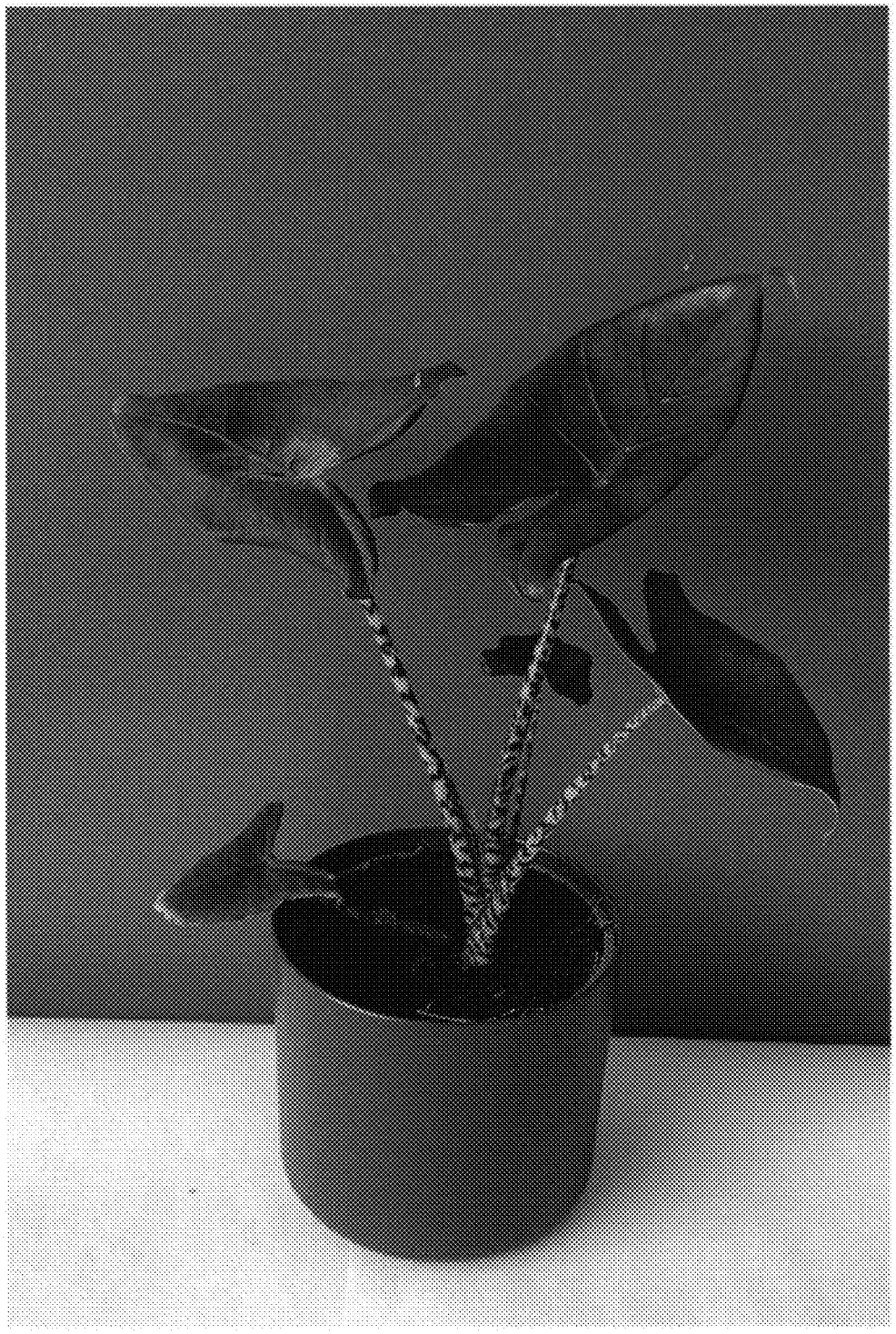

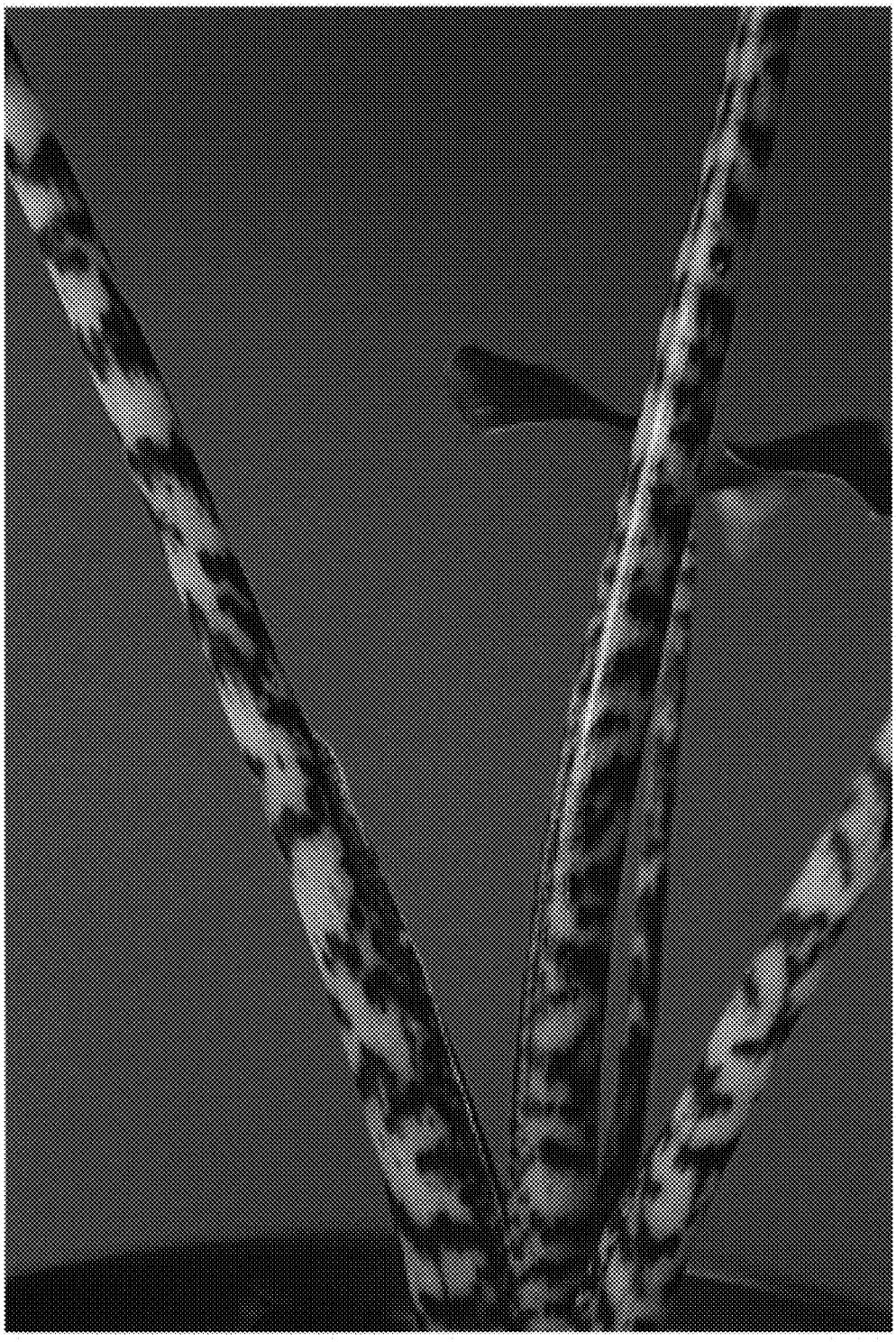

* * * * *